United States Patent [19]
Hoffer

[11] Patent Number: 4,750,499
[45] Date of Patent: Jun. 14, 1988

[54] CLOSED-LOOP, IMPLANTED-SENSOR, FUNCTIONAL ELECTRICAL STIMULATION SYSTEM FOR PARTIAL RESTORATION OF MOTOR FUNCTIONS

[76] Inventor: Joaquin A. Hoffer, Apt. 1204, 1540 29th Street, Calgary, Alberta, Canada, T2N4M1

[21] Appl. No.: 898,308

[22] Filed: Aug. 20, 1986

[51] Int. Cl.$^4$ .............................................. A61N 1/00
[52] U.S. Cl. .................................... 128/784; 128/421
[58] Field of Search .................. 128/419 R, 784, 642, 128/421, 422, 423 R, 423 W

[56] References Cited

U.S. PATENT DOCUMENTS

| | | | |
|---|---|---|---|
| 3,157,181 | 11/1964 | McCarty | 128/784 |
| 4,492,233 | 1/1985 | Petrofsky et al. | 128/421 |
| 4,590,946 | 5/1986 | Loeb | 128/784 |
| 4,602,624 | 7/1986 | Naples et al. | 128/784 |
| 4,630,611 | 12/1986 | King | 128/642 |

OTHER PUBLICATIONS

Solomonow, "External Control of the Neuromuscular System", 1984, IEEE Transactions on Biomedical Engineering, pp. 752-763.

Hansen, "EMG-Controlled Functional Electrical Stimulation of the Paretic Hand", Scandinavian Journal of Rehabilit. Medicine, 1979, pp. 189-193.

Crage, P. E. et al., Closed-Loop Control of Force During Electrical Stimulation of Muscle, IEEE Trans., BME 27:306-312, 1980.

Crage, P. E. et al., Control of Grasp by Force and Position Feedback, RESNA 9th Ann. Conf., Minneapolis, 1986.

Cybulski, G. R. et al., Lower Extremity Functional Neuromuscular Stimulation in Cases of Spinal Cord Injury, Neurosurgery, vol. 15, pp. 132-146, 1984.

Davis, L. A. et al., Compound Action Potentials Recorded From Mammalian Peripheral Nerves Following Ligation or Resuturing, J. Physiol. (1978), 285, pp. 543-559.

Gordon, T. et al., Long-Term Effects of Axotomy on Neural Activity During Cat Locomotion, J. Physiol., (1980), 303, pp. 243-263.

Hambrecht, F. T., Control of Neural Prostheses, Electromyography and Evoked Potentials, (1985), Ed. by A. Stuppler and A. Weindl, pp. 64-67.

Hoffer, J. A. et al., Implantable Electrical and Mechanical Interfaces with Nerve and Muscle, Annals of Biomedical Eng., vol. 8, pp. 351-360, (1980).

Hoffer, J. A. et al., Single Unit Conduction Velocities From Averaged Nerve Cuff Electrode Records in Freely Moving Cats, Journ. of Neuroscience Methods, vol. 4, pp. 211-225, (1981).

Hoffer, J. A. et al., A Method for Measuring Muscle Stiffness in Unrestrained Cats, Soc. Neurosci. Abstr., 9:470, (1983).

Hoffer, J. A. et al., Reflex Gain, Muscle Stiffness and Viscosity in Normal Cats, Soc. Neurosci. Abstr. 10: 330, (1984).

Hoffer, J. A., "Long-Term Peripheral Nerve Activity during Behavior in the Rabbit: the Control of Locomotion, Publ. 76-8530, University Microfilms, Ann Arbor, MI (1976).

Horch, K. W. et al., Long Term Adaptation of Cutaneous Type I and Type II Mechanoreceptors in the Cat, Chinese Journal of Physiological Sciences, 1985, 1(1), pp. 54-62.

Miyazaki, S. et al., Portable Limb-Load Monitor Utilizing a Thin Capacitive Transducer, J. Biomed. Eng., 1986, vol. 8, pp. 67-71.

Mortimer, J. T., Motor Prostheses, Chap. 5 in Handbook of Physiology, The Nervous System II, pp. 155-187, 1981.

Schoenberg, A. A. et al., Ultrasonic PVF$_2$ Transducers for Sensing Tactile Force, Ferroelectrics, vol. 60, pp. 239-250, (1984).

Primary Examiner—Lee S. Cohen
Assistant Examiner—Timothy G. Philips
Attorney, Agent, or Firm—Bertram I. Rowland; Steven F. Caserza

[57] ABSTRACT

An FES method for partially restoring the motor function of a person having paralyzed muscles, the method comprising implanting a force sensor comprising a nerve electrode for sensing electrical signals primarily from mechanoreceptors associated with a peripheral sensory nerve that supplies glabrous skin of the person having the paralyzed muscles; producing an electrical control signal for activating a muscle stimulator in response to the electrical signals sensed by the nerve electrode; and stimulating the paralyzed muscles in accordance with the control signal.

9 Claims, 2 Drawing Sheets

CLOSED-LOOP, IMPLANTED-SENSOR, FUNCTIONAL ELECTRICAL STIMULATION SYSTEM FOR PARTIAL RESTORATION OF MOTOR FUNCTIONS

BACKGROUND OF THE INVENTION

The present invention relates generally to functional neuromuscular stimulation (FNS) or functional electrical stimulation (FES) and, more particularly, to a closed-loop electrical control system for effecting and controlling such stimulation.

It is well known that spinal cord injuries can paralyze motor-function muscles by cutting off the transmission of neural information between the central nervous system and the peripheral nervous system in portions of the body below the level of the lesion in the spinal cord. Muscles used for motor functions can also be paralyzed by other types of events, such as cerebral vascular accidents.

It is also well known that partial restoration of the motor functions of such paralyzed persons can be achieved by functional electrical stimulation of the paralyzed muscles, in both upper and lower limbs. These FES systems use electricity to evoke a muscle response by the use of electrical stimulation as a substitute for the missing neural signals. The electrical stimulation can be effected by surface electrodes, percutaneous intramuscular electrodes, or implanted electrodes.

The electrical signals supplied to the stimulating electrodes in FES systems have been controlled by any of three different types of systems which are described in Cybulski, G. R., Penn, R. D. and Jaeger, R. J., "Lower Extremity Functional Neuromuscular Stimulation in Cases of Spinal Cord Injury", *Neurosurgery* 15:132–146, 1984. The first of these systems is an open-loop control system which permits the user to generate a command signal by means of a push button, rocker switch, hand-held manipulator or the like. The other two systems are both closed-loop control systems, one of which is referred to as "user-transparent", and the other as "supplemental sensory feedback".

In general, closed-loop control is preferred over open-loop control for both physiological and technological reasons. For example, there is a highly nonlinear relationship between the parameters which control the muscle stimulation and the resulting force and/or position output produced by the stimulated muscle. Moreover, the relationship between electrical stimulation of a muscle and the resulting output force is a time-dependent relationship. In open-loop systems the user must visually monitor the changes in force and/or position produced by the stimulation and adjust the command signal accordingly, and making these adjustments is both difficult and tedious. With closed-loop feedback control, however, the relationship between the input and output parameters can be automatically regulated to provide a linear relationship and to compensate for those effects which vary with time.

Closed-loop control systems for FES have been previously used only in laboratory experiments. In these systems, a sensor is required to produce the desired feedback signals in response to some physical consequence of the stimulation, such as force, position, stiffness or slip. For example, such feedback signals have been produced by the use of external sensors, i.e., sensors which are not implanted. External sensors, however, are typically difficult to calibrate, require frequent recalibration, are sensitive to environmental factors such as moisture and temperature, lead to breakage problems, and are bulky and unsightly and thus cosmetically undesirable.

SUMMARY OF THE INVENTION

It is a primary object of the present invention to provide a closed-loop FES system which can be fully implanted and thus eliminates the aforementioned shortcomings of the previous FES systems.

It is another important object of this invention to provide a closed-loop FES system using implanted force sensors which provide stable force feedback control signals.

Yet another object of this invention is to provide an improved closed-loop FES system which virtually eliminates the need for visual monitoring of performance, and consequent corrective adjustments, due to variations in the forces produced by the FES with changes in limb position and/or load.

Other objects and advantages will be apparent from the following detailed description and the accompanying drawings.

In accordance with the present invention, the foregoing objectives are realized by an FES system comprising stimulating means for stimulating praalyzed muscles; and implantable force sensor comprising a nerve electrode for sensing electrical signals primarily from mechanoreceptors associated with a peripheral sensory nerve that supplies glabrous skin of a person having the paralyzed muscles; and means responsive to electrical signals from the force sensor for producing an electrical control signal for activating the muscle-stimulating means.

DETAILED DESCRIPTION OF PREFERRED EMBODIMENT

Figure 1:
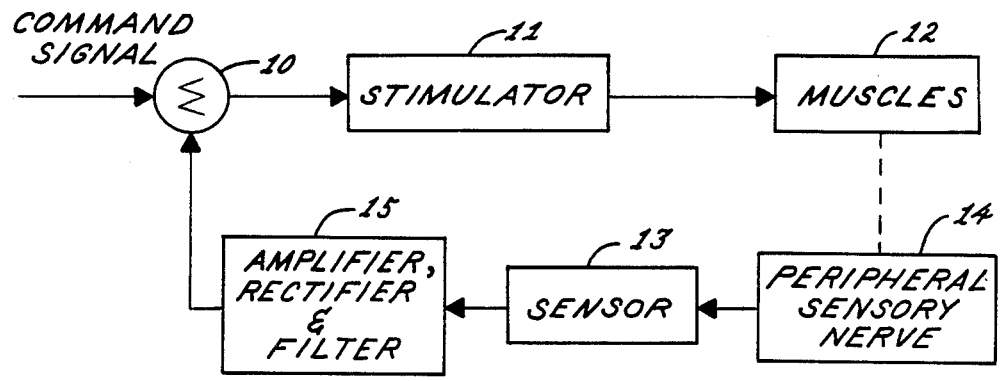
FIG. 1 is block diagram of an FES system in which the present invention cna be utilized.

Turning now to the drawings and referring first to FIG. 1, an electrical command signal is supplied to a summing junction 10 from a user-operated signal source, such as a push-button switch, a rocker switch or a hand-held manipulator. The junction 10 also receives a feedback signal (to be described below), and the algebraic sum of the two signals controls a stimulator 11 to activate one or more muscles to produce a desired motion or force. The stimulator 11 normally includes one or more electrodes in which electron flow is produced in response to the control signal from the junction 10, and this electron flow is converted to ion flow in the tissue adjacent the electrode. That is, the stimulator 11 produces an electric field which causes charges to flow through the electrode and the adjacent tissue, with the charges being carried by electrons in the metal electrode and by ions in the adjacent tissue. A rapid change in this electric field activates or stimulates muscle fibers, causing the production of action potentials that lead to muscle contraction and the production of force.

The electrical signals which stimulate the muscles normally have a prescribed frequency, pulse width and amplitude (typically a few milliamperes). These parameters are determined by conventional control circuitry included in the stimulator 11. This control circuitry is conventional, and a number of different stimulators containing such control circuitry are well known and described in the literature. The primary input to this control circuitry, of course, is the control signal produced at the output of the summing junction 10.

The stimulator 11 can activate the desired muscles either by stimulating the muscle fibers directly or by stimulating the motor nerves which in turn control muscle activation. The preferred stimulator uses implanted electrodes, i.e., electrodes implanted in the muscles 12 or on selected muscle-controlling nerves such as the femoral nerves, the sciatic nerves, or the gluteal nerves. Although the use of implanted-electrode stimulators is preferred, the present invention is not limited to the use of such stimulators and is also useful in FES systems using surface electrodes or percutaneous intramuscular electrodes as the stimulators. A variety of different stimulator electrodes are known in the literature. Recently proposed stimulators transmit the control signals to implanted electrodes by radio frequency so as to avoid the need for percutaneous connectors.

The feedback signal which is algebraically summed with the command signal at the summing junction 10 can compensate for errors in the command signal, and also can relieve the burden on the user by automatically regulating the stimulator in response to the actual output conditions such as the position of the limb controlled by the stimulated muscles and/or the force being exerted by the stimulated muscles. In the illustrative system of FIG. 1, the feedback signal is derived from a sensor 13 which detects signals from a peripheral sensory nerve 14. The output of the sensor 13 is passed through a circuit 15 that includes an amplifier, rectifier and filter, and then on to the summing junction 10.

The gain of the feedback loop must be sufficiently high to accommodate very small muscle forces, but not so high as to produce oscillations which would render the closed-loop system unstable. The illustrative feedback loop provides what is well known as "proportional" feedback control. It will be apparent, however, that the feedback signal may be further processed to provide other functions, such as "integral" or "derivative" feedback control. For example, an integrator can be added to the feedback loop to eliminate steady state errors, although the addition of such an integrator also reduces the response speed of the control system.

In accordance with an important aspect of the present invention, the feedback signals for the closed-loop FES system are provided by an implantable force sensor comprising a nerve electrode for sensing electrical signals primarily from mechanoreceptors associated with a peripheral sensory nerve that supplies glabrous skin of a person having paralyzed muscles. It has been discovered that a nerve electrode implanted in or around a peripheral sensory nerve associated with glabrous skin provides a signal which, when appropriately processed, is representative of the skin contact force. Such electrodes are often referred to as nerve "recording" electrodes, although in the present application they are more literally performing a sensing or detecting function.

Figure 2:
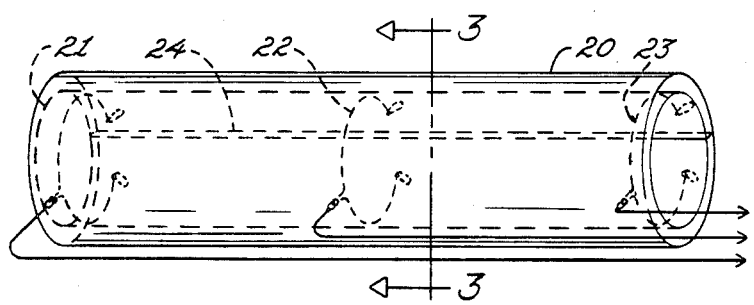
FIG. 2 is a perspective view of a preferred embodiment of a nerve cuff electrode for use in the invention.
Figure 3:
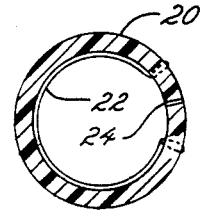
FIG. 3 is a section taken generally along line 3—3 in FIG. 2.

The preferred nerve electrode for this purpose is an implantable nerve cuff electrode, one example of which is illustrated in FIG. 2. This type of electrode surrounds the selected nerve in close proximity thereto, so that local current density changes associated with nerve impulses can be detected and read as voltage differences between the sensing electrode and a reference electrode. Close proximity of the electrode of the nerve cell axons or fibers is necessary because the conduction properties of the extracellular medium quickly attenuate the desired signals within a short distance of the source.

The nerve cuff electrode illustrated in FIG. 2 comprises a silicone rubber tube 20 having three circumferential electrodes 21, 22 and 23 spaced along the length of the tube. The electrode tube 20 is electrically insualting, and the electrodes are made of a biologically compatible conductive material such as stainless steel, platinum, iridium or carbon. The tube 20 is dimensioned to fit loosely around a selected nerve, and its length is preferably about ten times its inside diameter. The tube 20 and the circumferential electrodes 21-23 are slit longitudinally to permit the tube to be fit over the nerve; the slit 24 is closed with sutures after the tube is in place. The two end electrodes 21 and 23 are typically shorted to provide a reference potential. Neural signals near the center of the tube are then measured as voltage differences between the center electrode and the end electrodes. The use of dual reference electrodes helps to cancel longitudinal currents generated by sources other than the nerve fibers enclosed within the cuff (e.g., neighboring muscles or the heart). Of course, any desired number of electrodes may be utilized. Also, electrodes may be implanted directly in the nerve rather than using a cuff electrode.

The circumferential electrodes 21-23 are sewn to the inside wall of the rubber tube, and a lead from each electrode is passed radially through the wall of the tube and then longitudinally along the outside wall of the tube to a percutaneous connector leading to the external circuit 15. As an alternative to the percutaneous connector, the signals from the sensing electrode can be transmitted by an implanted radio frequency transmitter to an external receiver connected to the signal-processing circuitry.

Although the present invention is concerned primarily with force feedback control in an FES system, it will be appreciated that the force feedback can be used in conjuction with position feedback or other types of feedback control. Indeed, various position or combined position and force feedback control techniques for FES systems are already known in the literature.

Although the invention has been described above in connection with a closed-loop system utilizing analog circuits, it will be understood that the invention could also be implemented in digital systems. Thus, the voltage produced by the implanted nerve cuff electrode could be passed through an analog-to-digital (A/D) converter to produce a digital value which is supplied to a microprocessor. The microprocessor would also receive the command signal in the form of a digital value, algebraically sum the command signal value with the feedback signal value, and then perform any desired processing of the feedback signal value and/or the algebraic sum to product the desired control signal for the stimulator 11. For example, if it were desired to integrate the feedback signal before summing it with the command signal, the microprocessor would be programmed to carry out a mathematical integration using a series of digital values received from the A/D converter and stored in memory.

In a test conducted to determine the effectiveness of the present invention, cat footpads were used as a model of human glabrous skin. A silicone rubber cuff having a length of 30 mm and an insider diameter of 2.5 mm, and including three circumferential stainless steel recording electrodes (Cooner Wire AS 631), was implanted on the left tibial nerve just proximal to the ankle joint. The two end electrodes were shorted to each other and served as reference for differential recording at a gain of 20,000 and a bandpass of 1-10 kHz. This tripolar recording configuration and bandpass range were selected to reduce the pickup of unwanted EMG signals generated by surrounding muscles. The electrode impedances were about 5 kOhm. The viability of the tibial nerve was verified periodically from compound action potentials recorded from a second cuff electrode placed more proximally on the sciatic nerve. Compound action potentials and recorded neurograms were stable over the entire duration of the test, which was several weeks.

Depilatory cream was applied to the foot to reduce neural activity contributed by hairs. In addition, motor traffic recorded by the tibial nerve cuff was transiently eliminated by infusing lidocaine (2%) via a catheter connected to a 10 mm-long blocking cuff placed between the tibial and sciatic nerve recording cuffs. The completeness of the nerve conduction block was demonstrated by the disappearance of the sciatic cuff compound action potential. The electromyogram (EMG), force, length and temperature of triceps surae muscles were monitored with implanted transducers. The relations between triceps tendon force and the tibial nerve electroneurogram (ENG) were assessed as the cats walked on a treadmill. The relations between ENG, tendon force and ground contact force were further assessed as the cats stood unaided on four pedestals. One pedestal contained a vertical force sensor (Revere FT 50) and its position was controlled and could be unexpectedly changed by a computer.

Figures 4, 5:
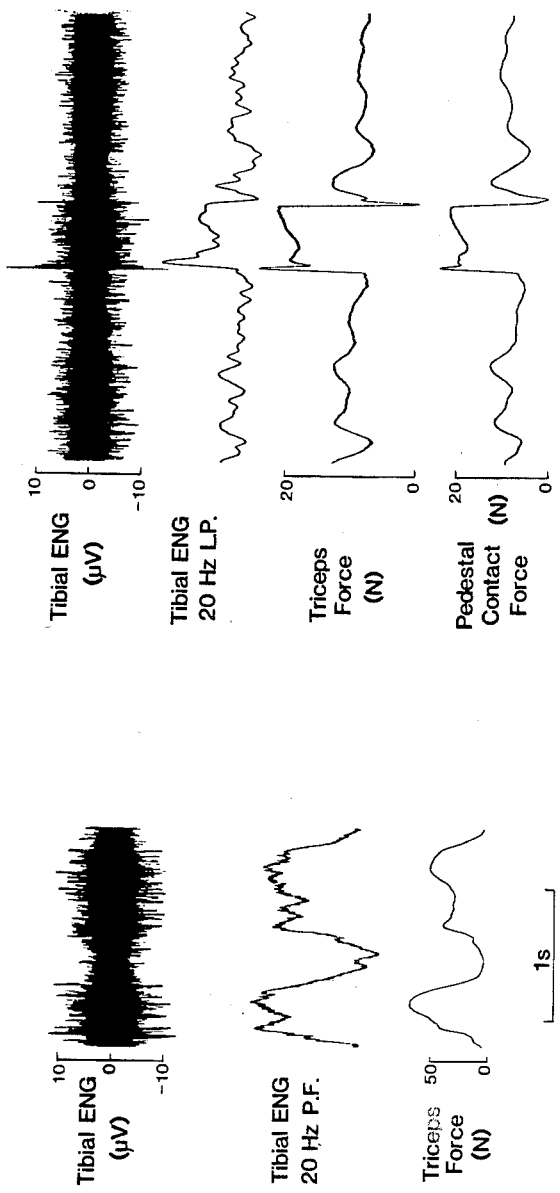
FIG. 4 is a set of data produced by an exemplary embodiment of the force sensor of the present invention.
FIG. 5 is another set of data produced by the same force sensor used to produce the data in FIG. 4.

Typical data recorded from a cat walking on a motorized treadmill are shown in FIG. 4. The electroneurogram recorded from the tibial nerve during walking modulated between $\pm 5$ and $\pm 10\mu$ V (the top trace in FIG. 4). For the purpose of comparison with force, the ENG was rectified and Paynter-filtered at 20 Hz (the middle trace in FIG. 4). The filtered tibial ENG closely resembled the triceps tendon force simultaneously recorded during walking (the bottom trace in FIG. 4). During the brief hesitation apparent midway through the second step, the filtered ENG accurately reflected the transient decline in the force recorded from the triceps tendon.

An example of a rapid postural adjustment in response to an unexpected upward movement of the pedestal supporting the left hindlimb is shown in FIG. 5. The filtered tibial neurogram (20 Hz low-pass cutoff), triceps force and vertical contact force recorded from the pedestal accurately followed each other. The rapid changes at onset of the perturbation and subsequent slower oscillations in force are clearly reflected in the tibial ENG.

During walking the filtered tibial ENG showed a somewhat faster rise time than the force (FIG. 4). This effect can be attributed to the dynamic properties of both the rapidly adapting and the slowly adapting skin mechanoreceptors. During rapid postural adjustments the rate of rise and the response at the onset of the perturbation were slower in the filtered ENG than in either the triceps tendon force or the pedestal contact force (FIG. 5). This was caused by the filter time constant selected (20 Hz).

In further experiments (not shown in the data of FIGS. 4 and 5) using a higher cutoff value (30 or 50 Hz), the transient force changes were more accurately reflected in the tibial ENG, but at the expense of a noisier signal. A comparison of the tibial nerve activity patterns during walking, with and without proximal block to eliminate motor traffic, revealed a small decline in the amplitude of modulation but no noticeable differences in the features of the modulated activity.

To verify that the tibial nerve cuff recordings did not pick up significant EMG activity generated by surrounding muscles, the tibial nerve was transected above and below the recording cuff. Under this condition, recordings during walking did not show modulations even though typical EMG patterns were still recorded from surrounding muscles. Spectral analysis also indicated that the frequency components of the intact tibial ENG and ankle extensor muscle EMG were essentially non-overlapping.

The present invention makes possible a closed-loop FES system which can be fully implanted and thus eliminate the shortcomings of previous FES systems. The implanted force sensor provided by this invention provides stable force feedback control signals which permit reliable control of a closed-loop FES system. This invention is intended to virtually eliminate the need for visual monitoring of performance, and consequent corrective adjustments, due to variations in the forces produced by the FES with changes in limb position and/or load.

What is claimed is:

1. An FES method for partially restoring the motor function of a person having paralyzed muscles, said method comprising:
   implanted a force sensor comprising a nerve electrode for sensing electrical signals primarily from mechanoreceptors associated with a peripheral sensory nerve that supplies glabrous skin of the person having the paralyzed muscles,
   sensing electrical signals via said force sensor,
   producing an electrical control signal for activating a muscle stimulator in response to the electrical signals sensed by said nerve electrode, and
   stimulating the paralyzed muscles in accordance with said control signal.

2. The FES method of claim 1 wherein said step of implanting a force sensor comprises the step of implanting a nerve cuff electrode.

3. The FES method of claim 2 wherein said nerve cuff electrode comprises an insulating tube disposed around a peripheral sensory nerve, and at least one electrode extending circumferentially around the inner surface of said tube.

4. The FED method of claim 1 wherein said electrical control signal is produced by generating a command signal, and algebraically summing said command signal and signals derived from the signals sensed by said nerve electrode.

5. An FES system for partially restoring the motor function of a person having paralyzed muscles, said system comprising:

an electrically controllable stimulator means for stimulating the paralyzed muscles, an implantable force sensor means comprising a nerve electrode for sensing electrical signals primarily from mechanoreceptors associated with a peripheral sensory nerve that supplies glabrous skin of the person having the paralyzed muscles and providing sensor signals in response thereto, and control means responsive to said sensor signals from said force sensor means for producing an electrical control signal for activating said stimulator means.

6. The FES system of claim 5 wherein said nerve electrode comprises a nerve cuff electrode.

7. The FES system of claim 6 wherein said nerve cuff electrode comprises an insulating tube adapted to be disposed around a peripheral sensory nerve, and at least one electrode extending circumferentially around the inner surface of said tube.

8. The FES system of claim 5 wherein said control means comprises:

means for generating a command signal, means for providing an algebraic sum signal by algebraically summing said command signal and said sensor signals, and means for producing said electrical control signal in response to said algebraic sum signal.

9. The FES system of claim 5 wherein said control means includes means for amplifying, rectifying and filtering the signals detected by said force sensor means.

* * * * *